(12) United States Patent
Bradley

(10) Patent No.: US 6,550,347 B2
(45) Date of Patent: Apr. 22, 2003

(54) VACUUM AIR COMPONENT SAMPLER

(76) Inventor: Bruce J. Bradley, 801 N. Lincoln, Jerome, ID (US) 83338

( * ) Notice: Subject to any disclaimer, the term of this patent is extended or adjusted under 35 U.S.C. 154(b) by 0 days.

(21) Appl. No.: 09/728,790

(22) Filed: Nov. 30, 2000

(65) Prior Publication Data

US 2002/0062702 A1 May 30, 2002

(51) Int. Cl.[7] .................................................. G01N 5/00
(52) U.S. Cl. ................................. 73/863.21; 73/863.23
(58) Field of Search ....................... 73/863.21, 863.22, 73/863.23; 96/413

(56) References Cited

U.S. PATENT DOCUMENTS

| | | | | |
|---|---|---|---|---|
| 2,489,893 A | * | 11/1949 | Johnsonq ..................... 183/26 |
| 3,977,254 A | * | 8/1976 | Brouwer .................... 73/422 R |
| 4,055,176 A | | 10/1977 | Lundquist ................... 128/214 |
| 4,092,845 A | * | 6/1978 | Prodi et al. ..................... 73/28 |
| 4,153,432 A | | 5/1979 | Beman et al. ................. 55/90 |
| 4,208,912 A | | 6/1980 | Baldeck ..................... 73/421.5 |
| 4,363,639 A | * | 12/1982 | Gladon ........................... 55/95 |
| 4,551,147 A | | 11/1985 | Mathieu et al. ............. 604/405 |
| 4,569,235 A | | 2/1986 | Conkle et al. ............ 73/863.03 |
| 4,936,878 A | | 6/1990 | Gustavsson et al. ........... 55/92 |
| 5,188,628 A | | 2/1993 | Rani et al. .................. 604/405 |
| 5,395,426 A | | 3/1995 | Huckins et al. ................ 95/44 |
| 5,551,311 A | | 9/1996 | Ogden et al. ............ 73/863.31 |
| 5,651,810 A | | 7/1997 | Flaherty et al. ............... 95/287 |
| 5,855,652 A | | 1/1999 | Talley ............................ 96/44 |
| 5,868,928 A | * | 2/1999 | Bradley .................... 210/257.2 |
| 5,902,385 A | | 5/1999 | Willeke et al. ............... 96/316 |
| 5,904,752 A | | 5/1999 | Willeke ....................... 95/216 |
| 5,954,845 A | | 9/1999 | Willeke et al. ............... 55/331 |
| 5,958,111 A | | 9/1999 | Willeke et al. ............... 95/268 |
| 5,967,332 A | | 10/1999 | Willeke ....................... 209/132 |
| 6,120,584 A | | 9/2000 | Sakata et al. ................. 96/135 |
| 6,123,751 A | | 9/2000 | Nelson et al. ................ 95/268 |

* cited by examiner

*Primary Examiner*—Hezron Williams
*Assistant Examiner*—Charles D Garber
(74) *Attorney, Agent, or Firm*—Robert L. Shaver; Frank J. Dykas; Stephen M. Nipper

(57) ABSTRACT

The invention is an air sampler which utilizes a hydrophobic filter and an entrapment fluid contained within a sampler body. Air to be sampled is bubbled through the entrapment fluid, which traps and retains a selected air component for later testing. Air which is thus bubbled through the entrapment fluid passes through a hydrophobic filter before leaving the sampler body. A hydrophobic filter prevents aqueous liquids from exiting the sampler body. This allows a higher rate of air flow, because the sampling fluid does not diminish as quickly due to suspended droplets exiting the sampler body. The sampler body may also be inverted to rinse down the walls of the sampler body without losing any liquid, due to the presence of the hydrophobic filter. The entrapment fluid can be poured or drained out of the sampler body.

4 Claims, 4 Drawing Sheets

VACUUM AIR COMPONENT SAMPLER

This invention was made with government support under a NIH grant, awarded by the National Institute of Health. The government has certain rights in the invention.

BACKGROUND OF THE INVENTION

1. Field of the Invention

The present invention generally relates to a method of collecting and concentrating airborne particles, organic or inorganic gasses and microorganisms, and more particularly to an apparatus for collecting airborne components by impinging or impacting them into a fluid or liquid entrapment media.

2. Background Information

Airborne particles are commonly collected by (a) inertial impaction onto selected surfaces, (b) centrifugal force resulting from spinning collected air such that particles are forced to an outside wall or medium for collection or (c) impingement into liquid where particles are intended to remain suspended in liquid after air bubbles pass through and out of the collection liquid.

The practice of impingement of biological particles into liquid during long-term (2 hours) aerosol collection periods has a distinct advantage over dry collection methods, in that microorganisms are not stressed or killed due to dehydration during continuously moving airflow, which removes moisture from the microbial cells.

However, low concentrations of particles collected from aerosols into fluids often require concentration in order to enumerate and quantitate these particles more accurately. This concentration step generally involves removal of the fluid from the collector followed by filtration of the fluid through separate equipment containing a small (0.45–0.2 micron) pore sized membrane in order to collect and concentrate the microorganisms. These extra fluid removal and filtration steps are disadvantages of prior art collection systems.

Another disadvantage of utilizing impinger methods to collect air particles, including bacteria, includes reaerosolization of microbes by air bubbles continuously flowing through the impacted collection fluid. As bubbles rise to the surface of the collection fluid, especially when utilizing aqueous liquids, the bubbles burst and send tiny droplets of water into the air above the collection fluid. These droplets can contain the microbes which the collection fluid was intended to collect and retain. As these droplets and entrapped microbes flow through the collection vessel and are deposited on the exhaust or effluent air channel walls, the microorganisms can be directly or indirectly re-introduced into the ambient air from which they were previously collected. Worse, the reaerosolized microbes could be introduced into previously clean air outside the sampling area depending on where the effluent air from the collection unit is exhausted. Additionally, as liquid or fluid molecules are continuously removed from the impinger by these processes, the decreased volume of fluid causes a concentrating effect on the remaining particles or organisms trapped therein and increased numbers of microbes or other particles are removed within the subsequent air bubbles and resultant droplets. Eventually, the impinger liquid or fluid level may be lowered below the air inlet tube nozzles or passages, thereby defeating the purpose of the apparatus. This loss of entrapment fluid thus shortens the operational life of the sampler.

It is an object of the invention to provide an air sampler which prevents recontamination of a sampling environment by release of contaminants from the air sampler in the form of water droplets with entrained contaminants.

It is another object of the invention to provide an air sampler which has an improved counting accuracy due to preventing escape with the outlet air of particles and contaminants, and being able to rinse down the inside of the sample chamber to recapture all sampled particles.

It is a further object of the invention to provide an air sampler which uses a liquid or fluid entrapment media, with or without additive or components such as antibodies to specific particles, attached or unattached to specific media such as Latex or polystyrene or other organic or inorganic beads or similar particles for specific of general entrapment of components, contaminants and particulates, which also has a longer run time than prior art air sampling devices which utilize a liquid or other fluid as an entrapment media.

It is a further object of the invention to provide an air sampler which enables a higher flow of air through the air sampler due to less loss of entrapment fluid through the air outlet.

An additional object of the invention is to provide an air sampler in which entrapment fluid in the air sampler is drained from the air sampler through a filter which is sized to capture particulates from the entrapment fluid.

SUMMARY OF THE INVENTION

In the apparatus of the present invention, a collection vessel is provided which allows a measured airflow which can contain airborne particles to be impinged through liquid or other entrapment fluid. The air sampler is designed to separate particulates and components from the air. The particulates can include all manner of microbes, including bacteria, yeast, mold, airborne parasites, single cell organisms, and viruses. The particulates can also include such things as inorganic or organic dust or debris, pollen, spores, weed seed, and powders. As the air is passed through the entrapment fluid, the entrapment fluid can be designed to absorb gases of interest, such as carbon monoxide, methane, carbon dioxide, oxygen, ethylene, nitrogen, or any number of organic or inorganic air gaseous contaminants, including poisonous gases used in chemical warfare. All of these substances, microbes, particulates and gases or related substances are described as air components.

The device of the invention is an air sampler for collecting selected air components which are suspended or carried in the air. The air sampler includes a sample body for entrapment of particles or components contained in air. It also includes an air intake for admitting air with entrained particles from a sampling environment into the sampler body. Contained within the sampler body is an entrapment fluid which serves to entrap, collect and retain or capture the selected air component. An impinger tube is utilized for bringing air into the sampler body and below the surface of the entrapment fluid, and for releasing bubbles of air through the entrapment fluid. As the bubbles rise from the impinger tube through the entrapment fluid, particles in the air are attracted to the liquid entrapment fluid or components thereof, and are adsorbed, in the case of particles, or absorbed in the case of gases into the entrapment fluid. Air from the impinger tube exists the entrapment fluid as the bubbles reach the surface and burst. The sampler body is provided with an air outlet which is located above the upper liquid level of the entrapment fluid. A pump is provided which evacuates air from the sampler body, through the air outlet. The decreased pressure of air thus created above the entrapment fluid causes air to be drawn in through the impinger tube and through the air intake to replace the evacuated air above the entrapment fluid.

A hydrophobic vent filter is positioned above the upper level of the entrapment fluid, over the air outlet, so that before air enters the air outlet, it must pass through the hydrophobic filter. The hydrophobic filter is designed to prevent water or other polar or aqueous liquid droplets, with their entrained particles, from exiting from the sampler body through the air outlet. The hydrophobic filter is designed so that only molecular water, in the form of water vapor, is allowed to exit the air sampler. The hydrophobic vent filter may be a Teflon coated fibrous filter, or other hydrophobic material, or coated material such as a polytetrafluoroethylene (PTFE), or PTFE coated fibrous filter, or other type of filter, or selective screening material which allows air but not aqueous liquids to pass. After air components have been collected in the sampler body, the entrapment fluid can be removed for testing. If the selected air component of interest are microbes, the entrapment fluid may be filtered through a very fine filter which will separate out the microbes but allow the entrapment fluid to pass. The filter may then be further tested for the particular microbe of interest. This may involve culturing the filter disk on a media such as selective or nutrient agar, so that microbe colonies can be counted after they have grown, or immersing the filter in liquid media for enrichment and subsequent application of bacterial detection methods. The nutritive agar ingredients would be varied to allow the growth of whatever microbe was of interest. Different detection and counting methods, chemical or physical, would be used for other particulates thus sampled, such as pollen, dust, or weed seeds. For sampling of gases which have been absorbed into the selected entrapment fluid or media, the entrapment fluid would be analyzed by a testing method for the particular gas or class of gases in question.

One version of the air sampler for contaminants includes a drain line from the sampler body. This drain line allows the entrapment fluid to be drained out of or otherwise removed from the sampler body. The drain line may further include a hydrophilic filter for retaining particulates in the entrapment fluid and separating these particulates from the entrapment fluid. A valve may be positioned on the drain line to activate the drainage or removal of entrapment fluid from the air sampler.

A prefilter may also be utilized which would have a large pore size compared to the particulates of interest. The prefilter would serve to remove particulates not to be tested from the air stream before the air stream entered the entrapment fluid. Such a prefilter can be hydrophilic or hydrophobic, depending on the sampling needs The sampler body may further include a sampling port in a side wall or other acceptable location of the sampler body. Entrapment fluid could be removed through the sampling port. Entrapment fluid thus removed could be tested for entrapped contaminants or particulates.

The air sampler described above would have a means for opening the sampler body for removal of entrapment fluid. One means for accomplishing this is having the sampler body made in two or more pieces, with a lid section or additional mid section which is detachable from the sampler body. A first clamp would be utilized to connect the two sections together, using o-rings to form a water- and air-tight seal. Additional clamps would be utilized for connecting additional sections of the sampler body.

If a prefilter is utilized in the air sampler, a filter support may also be utilized which would be mounted between the lid section and the sampler body. The sampler body can further be broken into three sections; a lid section, a mid section, and a base section. The first clamp connects the lid section to the mid section and a second clamp connects the base section to the mid section. Although a clamp is described as the mechanical mechanism for connecting the various sections of the sampler body, other means of connecting these sections can also be utilized. These could include friction fit connections, bayonet mounts, threaded connections, partial twist connections, and any conventional mechanical connection. O-rings or other devices for accomplishing a water- and air-tight seal would also be utilized.

The sampler body may also include a filter support for a hydrophilic filter mounted between the midsection and the base section described above.

The air sampler may further include a funnel which is mounted below the prefilter, and which channels air from the prefilter towards the entrapment fluid. The outlet tip of the funnel forms the upper portion of the air impinger tube. The air impinger tube may include a number of air passages, channels or nozzles which are located in the walls of the air impinger tube, for dispersing and releasing collected bubbles of air into the entrapment fluid.

One form of the device of the invention is an air sampler for sampling and collecting microbes or particulates in air. This version of the device of the invention includes a generally cylindrical sampler body which is formed from a detachable lid section, and a base section, in which a first clamp connects the lid section to the base section. An air intake is included for admitting air and entrained microbes or particulates from a sampling environment into the sampler body. An impinger tube is included with the side wall in which are defined one or more air channels for releasing air into the entrapment fluid. The air channels are located in the impinger tube below the upper liquid level of the entrapment fluid. An air outlet is provided through which is evacuated air from the sampler body above the entrapment fluid. A pump is provided for this movement of air from the sampler body. A filter support for a hydrophobic filter is provided between the lid section and the base section of the sampler body. A hydrophobic filter is provided which prevents liquid water and water or aqueous fluid droplets and their entrained microbes or particles from exiting from the sampler body through the air outlet. The hydrophobic filter allows only molecular water in the form of water vapor to exit the air sampler.

Another embodiment of the air sampler of the invention is a sampler with a generally cylindrical sampler body. The sampler body is comprised of a detachable lid section, at least one mid section, and a base section. A first clamp connects the lid section to the mid section, and the second clamp connects the base section to the mid section. As described above, any manner of mechanical connection which can be adapted to form a water- and air-tight seal is suitable for connecting these sections. An air intake is provided for admitting air from the sampling environment, into the sampler body. A prefilter support is provided for an optional prefilter which may be utilized to separate unwanted particulates from the air stream. An entrapment fluid is contained in the sampler body, for entrapment and retention of particulates in the air stream.

The prefilter would typically be a hydrophilic, fibrous filter through which air containing particulates is passed before it enters the entrapment fluid although certain hydrophobic filters could also be utilized as prefilters. An impinger tube is provided for directing sampled air and its suspended particulates into the entrapment fluid below the liquid upper level of the fluid. The impinger tube may optionally include one or more air passages or channels in the side walls for air bubbles to exit from the impinger tube into the entrapment fluid. Alternatively, the impinger tube could release air bubbles only at the end of the impinger tube. An air outlet is provided in the sampler body, through which air from the sampler body is evacuated. A pump or similar device is provided for evacuating air from the sampler body, and thus drawing air in the air intake and through the impinger tube. A hydrophobic filter support is provided between the mid sections and the base section, on which a hydrophobic filter is mounted. The hydrophobic filter is designed to prevent liquid phase water or other aqueous liquid and particulates entrapped in the droplets of liquid from exiting from the sampler body through the air outlet. The hydrophobic filter primarily allows only the passage of molecular water in the form of water vapor.

A drain line is provided from the sampler body for draining or removing the entrapment fluid. A valve opens the drain line and releases the entrapment fluid from the sampler body when the sampling period is finished. A hydrophilic filter support is provided with a second hydrophilic filter. This filter is sized to capture the desired particulates but to allow the passage of the entrapment fluid. When the valve is opened, entrapment fluid flows through the drain line and through the second hydrophilic filter. Entrapment fluid removal may be assisted by means of a vacuum air pump connected directly or indirectly to the drain line. The particulates of interest, which may be microbes or other particles, are captured on the second hydrophilic filter, and are made available for identification and enumeration after the entrapment fluid has been removed.

Still other objects and advantages of the present invention will become readily apparent to those skilled in this art from the following detailed description wherein I have shown and described only the preferred embodiment of the invention, simply by way of illustration of the best mode contemplated by carrying out my invention. As will be realized, the invention is capable of modification in various obvious respects all without departing from the invention. Accordingly, the drawings and description of the preferred embodiment are to be regarded as illustrative in nature, and not as restrictive.

DESCRIPTION OF THE PREFERRED EMBODIMENTS

Figure 1:
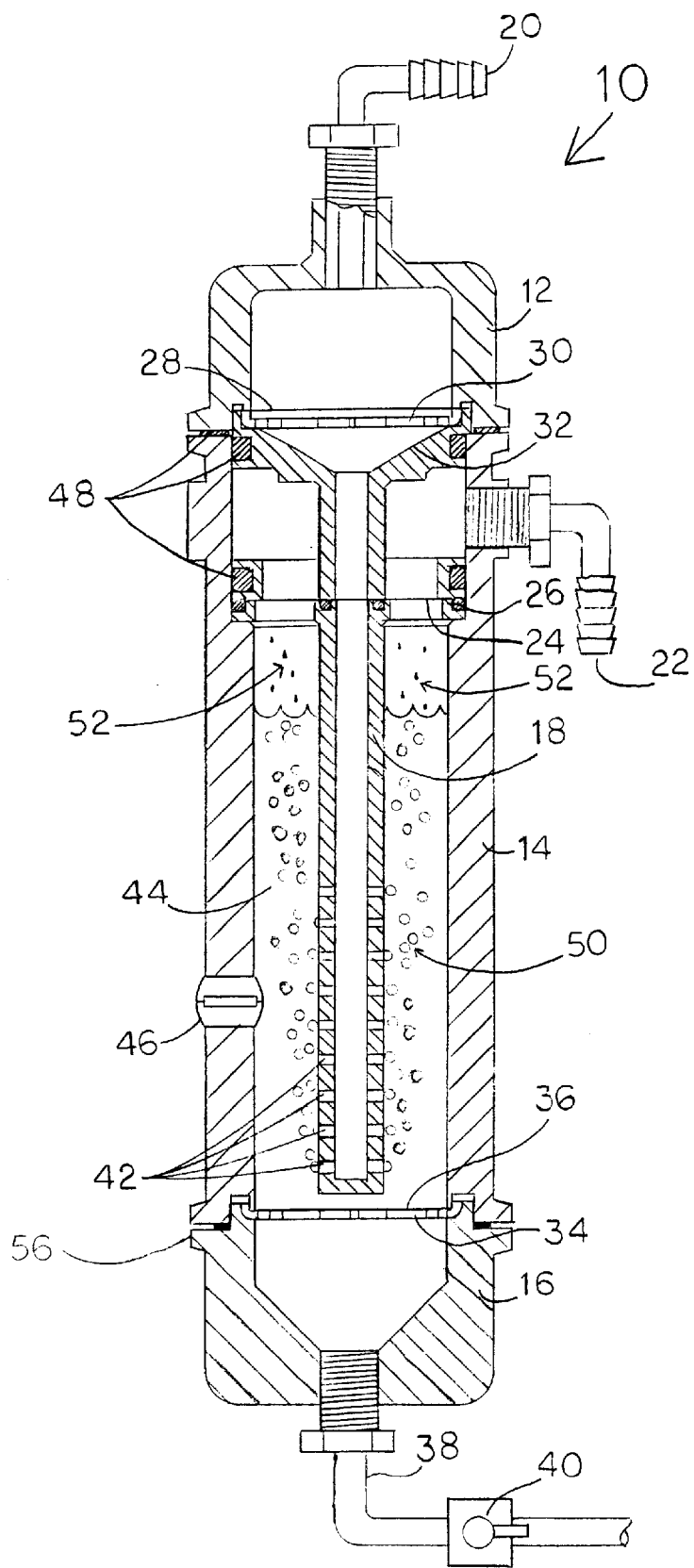
FIG. 1 is a side cross sectional view of an assembled air sampler of the invention.

While the invention is susceptible of various modifications and alternative constructions, certain illustrated embodiments thereof have been shown in the drawings and will be described below in detail. It should be understood, however, that there is no intention to limit the invention to the specific form disclosed, but, on the contrary, the invention is to cover all modifications, alternative constructions, and equivalents falling within the spirit and scope of the invention as defined in the claims.

Figure 2:
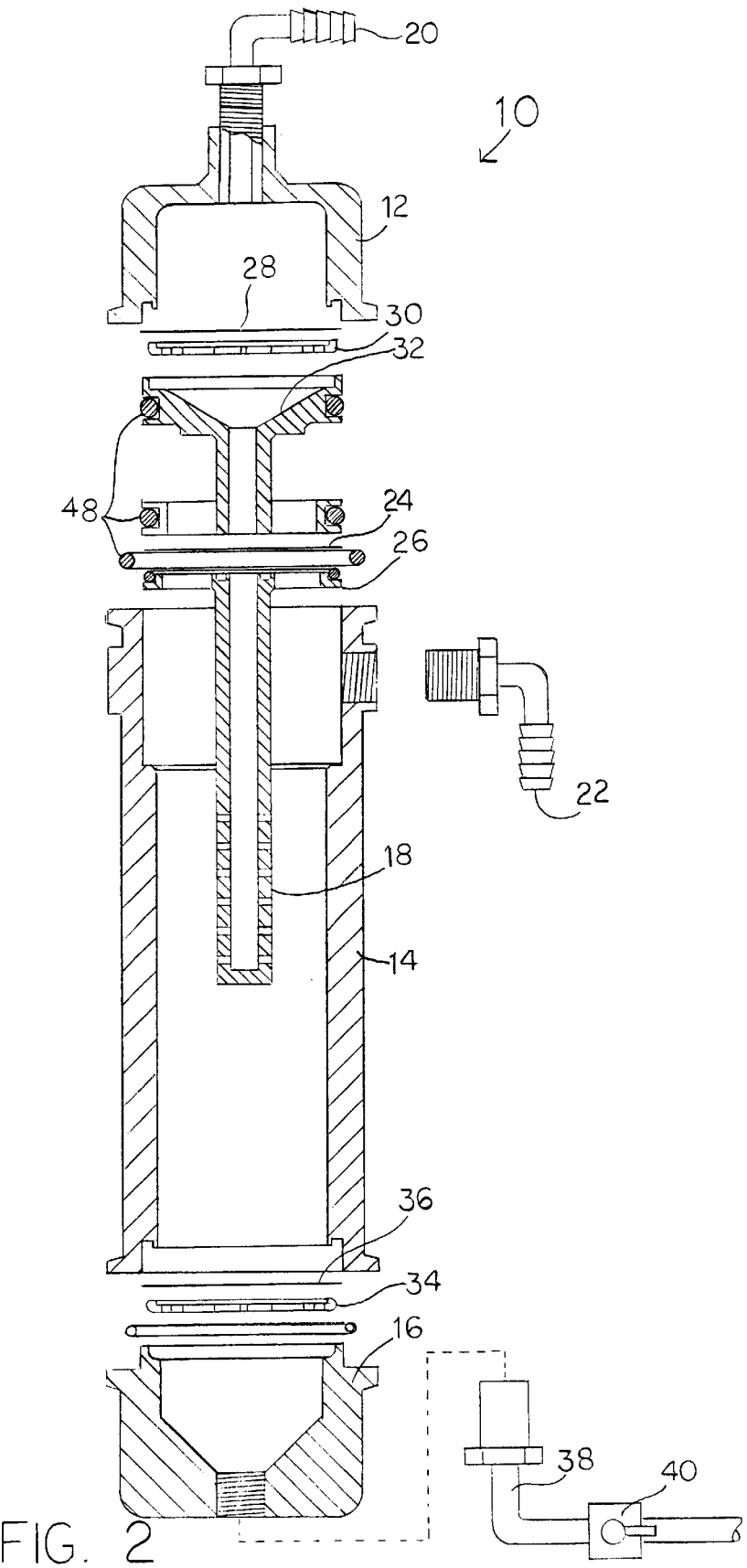
FIG. 2 is a side cross sectional view of the exploded parts of the air sampler.
Figure 3:
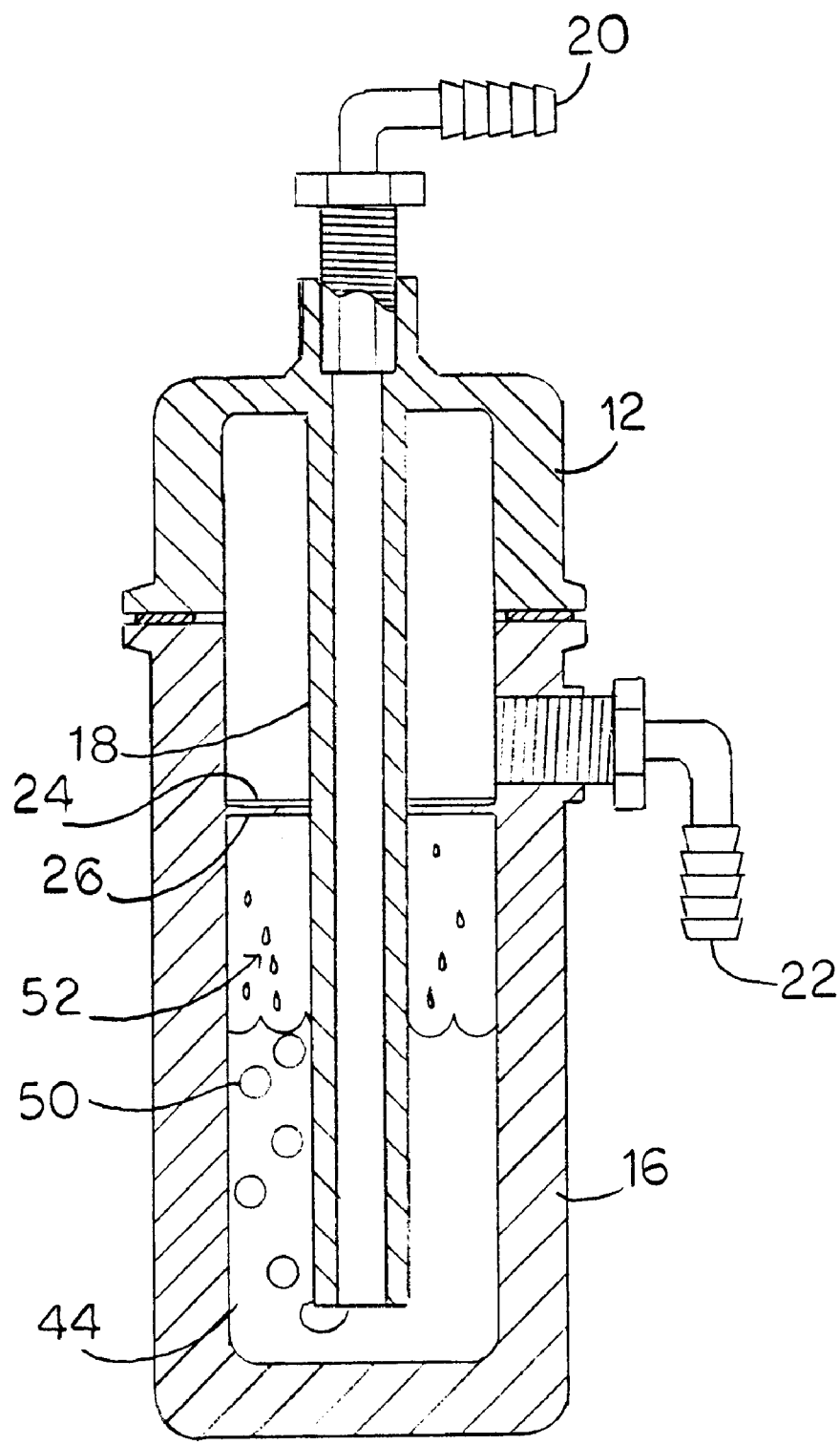
FIG. 3 is a cross sectional view of one embodiment of the air sampler of the invention.
Figure 4:
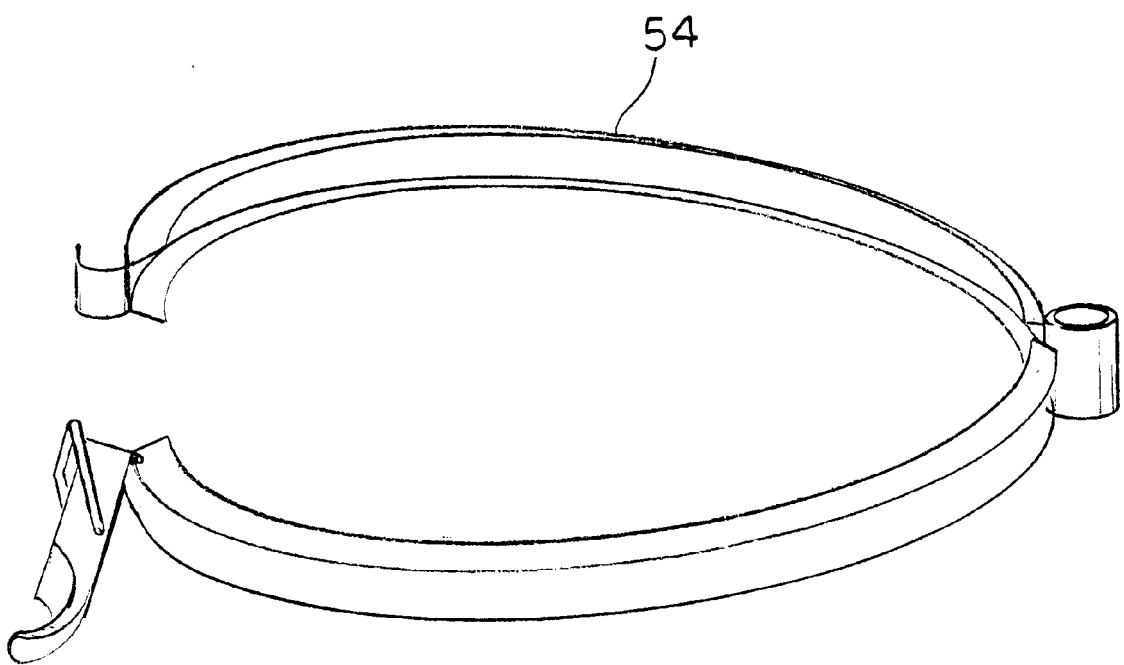
FIG. 4 is a top view of a clamp.

Several preferred embodiments of the invention are shown in FIGS. 1 through 4. FIG. 2 shows an exploded view of an air sampler of the invention. This air sampler is typically made of plastic, specifically, polycarbonate or similar. As shown in FIG. 2, the air sampler 10 is cylindrical in general shape, with walls which are approximately 3 to 6 millimeters thick, being increased in thickness as needed to accommodate certain clamps or threaded fittings. The air sampler 10 includes a lid section 12, one or more mid sections 14, and a base section 16. Each of these sections fit together and are attached to each other by the use of sealing ridges 56 which are held together by a clamp 54 shown in FIG. 4. Other means of attaching one section to another are also possible, and any conventional joining means is also suitable. This can be by the use of threaded sections, by a partial twist locking mechanism, by friction fit, by the use of screw or bolt-together joints, and by the use of any number of clamps which hold the section together. Another preferred method of holding the sections together is to have the air sampler molded together with the sections joined with plastic welds or similar connections. Some of these section junctions will be designed as "break" joints, which can be squeezed with a user's fingers and caused to break apart. These break joints are used commonly in devices currently made by other filter manufacturers.

In this preferred embodiment of the invention, the lid section 12 is approximately 1½ inches in inside diameter and ½–1 inches tall. The midsections 14 are approximately 1½ inches in diameter and 5–8 inches tall. Base section 16 is 1½ inches in inside diameter and 1½ inches tall. Where the lid section 12 and the mid section 14 join, a prefilter support 30, and a prefilter 28 may be optionally located. The prefilter support 30 is a grid with large openings which does not impede the passage of air or particulates. The prefilter is a fibrous, circular membrane with pores which are sized according to the needs of the sampling situation. In some sampling situations a prefilter would not be required at all. In other sampling situations, the prefilter may have pores which are approximately 40 microns in size. Located below the prefilter is funnel 32. The funnel 32 is approximately 1½ inches in diameter and 1½ inch long. Since it is located directly below the prefilter, air which passes through the prefilter is directed into the funnel. The lower end of the funnel stem forms or connects to the beginning of an impingement tube 18. In this embodiment of the invention, the impingement tube 18 includes air channels, passages or nozzles 42. The funnel 32 lower stem end and the impingement tube 18 form an air tight connection when the two are nested together upon assembly of the air sampler, as shown in FIG. 1. At the joint between mid sections 14 and base section 16, a second filter 36 and a second filter support 34 is located. The second filter 34 would typically be a hydrophilic filter, and would have a pore size of 0.2–0.45 microns. The base section 16 is attached to a drain line 38 which includes a valve 40.

FIG. 1 shows the assembled device, with the addition of entrapment fluid 44 filling a portion of the mid sections 14 and the base section 16. For many microbes, the entrapment fluid would be Butterfield's Phosphate Buffer or phosphate buffered saline with or without additives such as glycerin or other microbial preservatives or stress reduction agents. The entrapment fluid may contain a combination of fluids or gels, beads, ionic exchange salts and various chemical compounds in a wide range of concentrations which could be used to capture gases or chemical or physical particles as well as microbes and pollen.

Very small polystyrene beads (Latex) or other materials, some of which are called magnetic beads, can be coated with antibodies which will bind to and hold specific bacteria (and probably any other protein such as pollen grains) within a buffer solution for example. These beads could be large enough to be filtered out on the sampler's final filter (base filter) then could be separated or concentrated further for identification of specific bacteria. The air sampler could, in theory, have an entrapment fluid which contained these beads for specific bacteria or other components. The fluid could be "poured" out then centrifuged after the collection period to concentrate these beads and attached components then processed with the magnets, etc. for more specific identification. The entrapment fluid or media may comprise specifically or generally aqueous liquids or buffer solutions of all types, ionic exchange resins, cationic or anionic, or organic components and mixtures such as enzymes, antibodies and antigens or other proteins or binding components, attached or unattached to carrier-compounds or substances such as polystyrene beads or similar inert materials, and laboratory reagents of specific or general binding characteristics including inorganic or organic acids or bases and mixtures of specific inorganic or organic elements or compounds, which physically or chemically bind or otherwise temporarily or permanently capture air components. If the entrapment fluid is an organic alcohols or acids, or another chemical which is incompatible with plastic, the sampler body may be made of stainless steel, glass, quartz, or another material designed not to be corroded by the entrapment fluid.

In use, the device would be assembled as shown in FIG. 1. A pump (not shown) would be attached to the air outlet 22 and when activated would evacuate air from the chamber in mid sections 14 which is above the upper liquid level of the entrapment fluid 44, and which is above the hydrophobic membrane 24.

Mounted in the upper mid section 14 is a hydrophobic filter support 26 and a hydrophobic filter 24. The hydrophobic filter 24 has a typical pore size of one micron, and is typically fibrous, and coated with Teflon or related hydrophobic material, specifically, Polytetrafluoroethylene (PTFE). In one preferred embodiment, the hydrophobic filter is circular with a hole in the middle, and is a catalog number J100A047A Teflon filter of PTFE coated filter, with a 1.0 micron pore size, made by Micro Filtration Systems, Inc. and custom cut to allow for passage of the funnel stem 32. It is constructed so that no liquid water or water or other aqueous media droplets can pass through the Teflon filter coating. However, water vapor, in the form of molecular water can pass through the pores of the filter. This arrangement allows a high flow of air through the hydrophobic filter 24, but does not allow liquid water or other aqueous media to pass through the filter. This filter would typically be PTFE or a fibrous filter coated with PTFE or other hydrophobic material or Teflon-coated material such as PTFE coated selective screening material. Other names for PTFE include Polytef, Fluon, Fluoroflex, Teflon, and polytetrafluoroethylene resins. Other compounds with similar hydrophobic properties would be suitable alternatives. If a non-aqueous or non-polar chemical is used as the entrapment fluid, a material which does not allow the passage of liquid entrapment fluid would be used in place of the hydrophobic filter.

As air is evacuated in the region of the mid sections 14 above the hydrophobic filter 24, air is pulled through the hydrophobic filter 24. As air in this space is evacuated, air is drawn through the impingement tube 18, from the interior of the lid section 12 and through the air inlet 20. Unwanted particulates may optionally be filtered out of the inflowing air at the prefilter 28. It should be noted that prefilter 28 is optional, and may not be utilized or necessary in certain sampling applications. As air is drawn into the mid sections 14 through the impingement tube 18, it leaves the impingement tube through air channels 42 in the side wall of the impingement tube 18. The air passes through the entrapment fluid 44 as bubbles 50 as shown in FIG. 1.

As the bubbles reach the surface of the entrapment fluid, they may carry or eject small water droplets 52 into the air above the entrapment fluid 44. This is similar to the mechanism seen in prior art, and in prior art can lead to the water droplets 52 and entrained particulates and other contaminants and air components exiting with the water droplets through the air outlet 22. However, in the device shown in FIG. 1, the water droplets 52 with their entrained particulates, contaminants, or air components cannot pass through the hydrophobic filter 24. Thus, all of the air components are retained in the entrapment fluid unless they leave as a gas or in other molecular form not prevented by the hydrophobicity and pore size of the hydrophobic filter. This allows the hydrophobic filter and the walls of the container in which the entrapment fluid is enclosed to be washed down by tilting the air sampler 10 in order to dislodge all of the air components to be sampled which may be sticking to the walls or the hydrophobic filter 24 and support 26. After a period of time, the entrapment fluid 44 may be removed for testing. The testing method would be tailored to identify and enumerate the air component of interest. One air component which might be frequently sampled would be microbes which are suspended in the air with or without attachment to other particles. These microbes would include bacteria, mold, yeast, viruses, airborne pathogens, and single celled organisms. Other air components which would be sampled might include vegetative spores, pollen, weed seeds and dust, organic or inorganic. Another air component which might be sampled could be gases in the air, such as carbon dioxide, methane, ethylene, or any inorganic or organic component of the air, including poisonous gases and powders. Each of these components would have a different testing mechanism.

One method of removing the entrapment fluid 44 from the air sampler 10 would be to remove the lid and upper mid section, and simply pour the entrapment fluid 44 out like a cup. The embodiment shown in FIG. 1 also has a sampling port 46, which can be accessed either to add or remove entrapment fluid, and this could be done periodically even while the air sampler is in operation. A drain line 38 is also provided, with a valve 40. When valve 40 is opened, the entrapment fluid in the air sampler 10 exits the air sampler 10 through the second filter 36 assisted by a pump if needed or desired. If this is sized appropriately, the second filter 36 would stop the particulate of interest, such as microbes. If the air sampler 10 is used to sample air for microbes, the second hydrophilic filter 36 could be removed and placed on growth media such as selective or nutrient agar to grow out the entrapped microbes for identification and counting, or for testing with various rapid microbial detection methods such a immunoassays or DNA-related tests such as polymerase chain reaction assays.

FIG. 3 shows another preferred embodiment of the air sampler 10. The air sampler 10 of FIG. 3 is a simplified version, and does not contain prefilters or even a second hydrophilic filter. It does contain an air inlet 20, and air outlet 22, a lid section 12 and base section 16. Enclosed within the base section 16 is entrapment fluid 44. Attached to the air inlet 20 is an impingement tube 18. As in the previous version, air is evacuated above a hydrophobic filter 24, which causes air to be drawn in the inlet tube 20 and bubbles out the impingement tube 18 into the entrapment fluid 44. Droplets 52 are not allowed to enter the air outlet 22. This version of the device may be opened and the liquid poured out, or removed by pipetting. Both of the previous embodiments show a hydrophobic filter 24 which is mounted so that it surrounds the funnel 32 stem and impingement tube 18. A design requirement is that the hydrophobic filter 24 have sufficient surface area to allow for a high volume of air flow, assuming a high volume of air flow is desired. The hydrophobic filter 24 could be mounted in other ways, such as on the side wall of one of the sampler body sections, covering the air outlet 22. The air outlet 22 could also be mounted in the lid section of this embodiment.

While there is shown and described the present preferred embodiment of the invention, it is to be distinctly understood that this invention is not limited thereto but may be variously embodied to practice within the scope of the following claims.

From the foregoing description, it will be apparent that various changes may be made without departing from the spirit and scope of the invention as defined by the following claims.

I claim:

1. An air sampler for use with an air pump for sampling air, comprising:
   - a sampler body for collecting selected air components with a mid and a base section;
   - an air intake for admitting air and air components from a sampling environment into said sampler body, driven by said air pump;
   - an entrapment fluid contained in said sampler body, for entrapment of said selected air components;
   - an impinger tube for impinging air into said entrapment fluid;
   - an air outlet, which provides a route for air to exit said sampler body, driven by said air pump;
   - a hydrophobic filter, positioned to prevent loss of entrapment fluid from said air sampler, for preventing liquid and entrained contaminants from exiting said sampler body through said air outlet, in which the hydrophobic filter is a polytetrafluoroethylene;
   - a particulate filter for capturing air components and separating said air components from said entrapment fluid for testing and quantitation; and
   - a filter support for said particulate filter for said particulate filter between said mid section and said base section.

2. An air sampler for sampling air use with an air pump for sampling air, comprising:
   - a sampler body for collecting selected air components, with a detachable lid section and a first clamp for connecting said lid section to said sampler body;
   - an air intake for admitting air and air components from a sampling environment into said sampler body, driven by said air pump;
   - an entrapment fluid contained in said sampler body, for entrapment of said selected air components;
   - an impinger tube for impinging air into said entrapment fluid;
   - an air outlet, which provides a route for air to exit said sampler body, driven by said air pump;
   - a hydrophobic filter, positioned to prevent loss of entrapment fluid from said air sampler, for preventing liquid and entrained contaminants from exiting said sampler body through said air outlet, in which the hydrophobic filter is a polytetrafluoroethylene;
   - a particulate filter for capturing air components and separating said air components from said entrapment fluid for testing and quantitation; and
   - a filter support for said particulate filter mounted between said lid section and said sampler body.

3. An air sampler for sampling air components, comprising:
   - a generally cylindrical sampler body with a detachable lid section, at least one detachable mid section and a detachable base section, in which a first clamp connects said lid section to said mid section, and a second clamp connects said base section to said mid section;
   - an air intake for admitting air and air components from a sampling environment into said sampler body;
   - an entrapment fluid contained in said sampler body, for entrapment of said air components;
   - an impinger tube for passing air bubbles through said entrapment fluid, with said impinger tube including a side wall which defines one or more air passages;
   - an air outlet, for evacuating air from said sampler body;
   - a pump for evacuating air from said sampler body;
   - a hydrophobic filter support for a hydrophobic filter mounted operatively between said entrapment fluid and said air outlet;
   - said hydrophobic filter for preventing liquid phase aqueous fluid and entrained air components from exiting said sampler body through said air outlet;
   - a drain line from said sampler body for draining said entrapment fluid;
   - a valve for opening said drain line and releasing said entrapment fluid from said sampler body; and
   - a hydrophilic filter support and a hydrophilic filter mounted operatively to filter said entrapment fluid as it is drained from said sampler body, for capturing particulate contaminants and separating said particulate contaminants from said entrapment fluid.

4. An air sampler for use with an air pump for sampling air, comprising:
   - a sampler body for collecting selected air components;
   - an air intake for admitting air and air components from a sampling environment into said sampler body, driven by said air pump;
   - an entrapment fluid contained in said sampler body, for entrapment of said selected air components;
   - an impinger tube for impinging air into said entrapment fluid;
   - an air outlet, which provides a route for air to exit said sampler body, driven by said air pump;
   - a hydrophobic liquid blocking filter positioned before said air outlet, for preventing aqueous liquids and entrained contaminants from exiting said sampler body through said air outlet;
   - a sampling port in a said sampler body, for adding entrapment fluid, or withdrawing entrapment fluid and entrapped air components for testing; and
   - a funnel connected to said air impinger tube, which carries air from said air impinger tube.

* * * * *